United States Patent [19]

Sapienza

[11] Patent Number: 5,376,081
[45] Date of Patent: Dec. 27, 1994

[54] OPAQUE SYRINGE

[76] Inventor: Salvatore Sapienza, Via Trieste, 8, Pedara, Catania, Italy

[21] Appl. No.: 805,882

[22] Filed: Dec. 11, 1991

[30] Foreign Application Priority Data

Mar. 25, 1991 [IT] Italy .......................... MI91 U 000248

[51] Int. Cl.⁵ .................................................. A61M 5/00
[52] U.S. Cl. ........................................ 604/207; 604/186; 604/218
[58] Field of Search ............... 604/110, 187, 186, 207, 604/208, 218, 228, 239, 240, 246

[56] References Cited

U.S. PATENT DOCUMENTS

| | | | |
|---|---|---|---|
| Re. 25,113 | 1/1962 | Wilburn . | |
| 145,217 | 12/1873 | Leiter | 604/218 |
| 235,953 | 12/1880 | Lefferts . | |
| 600,803 | 3/1898 | Robinson et al. . | |
| 637,405 | 11/1899 | Papendell | 604/208 |
| 767,686 | 8/1904 | Detmers | 604/218 |
| 1,559,978 | 11/1925 | Page | 604/186 |
| 1,652,894 | 12/1927 | Gunther | 604/207 |
| 2,432,605 | 12/1947 | Barach | 604/207 |
| 2,515,956 | 7/1950 | Greenberg | 604/207 |
| 2,658,511 | 11/1953 | Furnell | 604/218 |
| 3,234,944 | 2/1966 | Stevens et al. | 604/240 |
| 3,459,177 | 8/1969 | Deuschle | 604/187 X |
| 3,907,009 | 9/1975 | Dobbins | 604/207 X |
| 4,048,997 | 9/1977 | Raghavachari et al. . | |
| 4,466,426 | 8/1984 | Blackman . | |
| 4,921,277 | 5/1990 | McDonough | 283/81 |
| 5,009,645 | 4/1991 | Silver et al. | 604/207 |

FOREIGN PATENT DOCUMENTS

| | | | |
|---|---|---|---|
| 9324 | 10/1902 | European Pat. Off. | 604/207 |
| 0041969 | 8/1807 | Switzerland | 604/207 |
| 0279779 | 3/1952 | Switzerland | 604/207 |
| 0701232 | 12/1953 | United Kingdom | 604/207 |
| 1212823 | 11/1970 | United Kingdom | 604/208 |

Primary Examiner—C. Fred Rosenbaum
Assistant Examiner—V. Alexander
Attorney, Agent, or Firm—Young & Thompson

[57] ABSTRACT

A syringe comprising a completely opaque barrel (2) and a plunger (3) having at least two measuring scales (6, 6'; 7, 7'), wherein one scale includes ascending numeral values and the other includes descending numeral values having a common index made of a rectilinear end (8) of the base of the cylinder.

6 Claims, 2 Drawing Sheets

OPAQUE SYRINGE

FIELD OF INVENTION

The present invention relates to a syringe constructed of opaque material, which can be used both as a hypodermic syringe and a pump and is suitable for providing total protection against light to the substance contained therein.

Many medicinal substances are known, which are used for example in chemotherapy when treating tumors, having a tendency to rapidly alter if exposed to light, thus loosing their therapeutic effect.

DESCRIPTION OF RELATED ART

Various different forms of opaque or opaque shielded syringes or pumps equipped with longitudinally spaced measuring indicia heretofore have been provided such as those disclosed in U.S. Pat. Nos. 235,953; 600,803; 4,048,997; 4,466,426 and Re. 25,113. However, these previously known forms of syringes do not include the measuring indicia of the instant invention of both the ascending and descending type and wherein diametrically opposite quadrants of the plunger of the syringe include, respectively, right hand readable and left hand readable indicia.

U.S. Pat. No. 235,953 does not provide a syringe which is opaque to actinic radiation and further does not disclose a syringe including both ascending and descending measuring indicia readable from either side of the syringe barrel.

U.S. Pat. No. 600,803 does not disclose an inexpensive hypodermic syringe which may be marketed in sterilized condition and as a throw-away device, inasmuch as the syringe is constructed of expensive metals. Further, the small, hair-like peripheral grooves provided on the plunger of the syringe are very difficult for the user to use in measuring dosage.

U.S. Pat. No. 4,048,997 discloses a syringe constructed of transparent glass, but covered with a thin resin film which inhibits the transmission of actinic light while passing other light in the visible spectrum. However, it is important in many cases not to merely inhibit the transmission of actinic light, but to totally block out all visible light. Still further, the thin resin film provided is subject to being scrapped off accidentally to thereby destroy the actinic light blocking capacity thereof, and in fact this patent also teaches purposely removing at least a part of the protective film to facilitate visual inspection of the syringe contents prior to use. Also, removal of part of the protective film requires a use of two hands of the user while a syringe not designed to have a portion of a protective layer removed therefrom may be readily operated by one hand.

U.S. Pat. No. 4,466,426 discloses a syringe with an actinic ray blocking stripe, but this syringe includes additional parts rendering it more expensive to produce. Further, providing an actinic ray blocking stripe on a syringe barrel is more expensive than providing a hypodermic syringe constructed of opaque material for totally blocking actinic rays. Also, by providing only an actinic ray blocking stripe on a portion of the barrel of a syringe, actinic rays may enter the interior of the syringe barrel through portions of the syringe barrel not covered by the applied stripe. Further, the syringe disclosed in U.S. Pat. No. 4,466,426 does not provide measuring indicia (both ascending and descending) of a readily readable type and readily viewable from either side of the syringe. Thus, the dosage indicia is difficult to understand and read. Also, this syringe is designed for use by diabetics and is primarily concerned with providing tactile and/or auditory indication of dosage position of the plunger relative to the barrel. Still further, this syringe must be constantly oriented in a manner such that the ray blocking means thereof is uppermost.

Finally, U.S. Pat. No. Re. 25,113 discloses a syringe which includes descending indicia as medication is administered therefrom, but which does not also disclose ascending measuring indicia. Further, the provided indicia must be read with the barrel end of the syringe uppermost and may not be readily read from either side of the barrel. Still further, this syringe includes a great number of parts and the material of which the syringe is constructed must be relatively thin and transparent in order to be clearly seen through. It is also pointed out that this syringe includes dosage measuring and indicating means which are sufficiently complex to require more than minimal training in the usage thereof, thereby limiting the health care professionals which may dependably utilize the syringe.

OBJECT OF THE INVENTION

The main aim of the present invention is to eliminate the above-mentioned inconveniences, by providing a syringe which gives its content total protection against light without increasing production costs with respect to a traditional syringe.

A further aim of this invention is to directly provide the user with a progressive visual indication of the amount of injected substance as well as of remaining substance, and vice versa, in case of drawings from the body of the patient.

BRIEF SUMMARY OF THE INVENTION

According to the present invention the above aims are achieved by means of a completely opaque syringe barrel, namely non transparent to light, and also by providing the plunger rod with at least a pair of measuring scales, one ascending and the other descending, whose index can be for example the rectilinear end of the cylinder opposite to the tip end. Accordingly, in whatever position of the plunger, two values can be read on the two measuring scales, whose sum is always the maximum value of each measuring scale, e.g. 5 ml in a 5 ml syringe.

In a preferred embodiment of the syringe according to the invention, two pairs of measuring scales are provided on the syringe in order to be easily readable also by left handed persons.

Further features of the present invention will be clearer from the following detailed description, which gives a non limitative example of realization, reference being made to the accompanying drawings forming a part thereof.

DETAILED DESCRIPTION OF THE INVENTION

Figure 1:
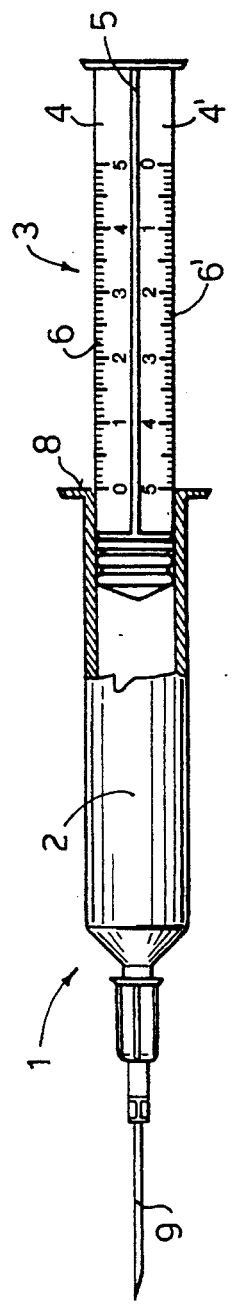
FIGS. 1, 2 and 3 show a 5 ml hypodermic syringe according to the invention in three different positions of the plunger.

In the description of the embodiments shown in the attached Figures the same numerals will be used to refer to like or corresponding parts.

Referring firstly to FIGS. 1 to 4, FIG. 1 shows a syringe for injections provided with a barrel 2 which slidingly receives a plunger having a cross type section, namely provided with four flat wings 4, 4', 5, 5', placed at 90° with respect to one another.

According to the present invention the barrel 2 is completely opaque, namely non transparent to light, in order to protect the medicinal substance contained therein against light rays. Two measuring scales 6, 6', one made of numerals ascending from 0 to 5 ml and the other made of numerals descending from 5 to 0 ml, are placed in whatever possible way on two aligned wings 4, 4' of the plunger 3, for example through incision, colouring or application of adhesive strips. The rectilinear end 8 of the base of barrel 2 provides a common index for the two scales.

Figure 2:
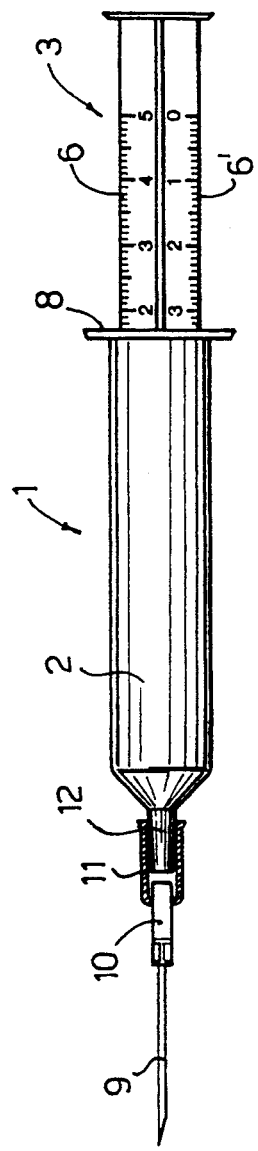
Figure 3:
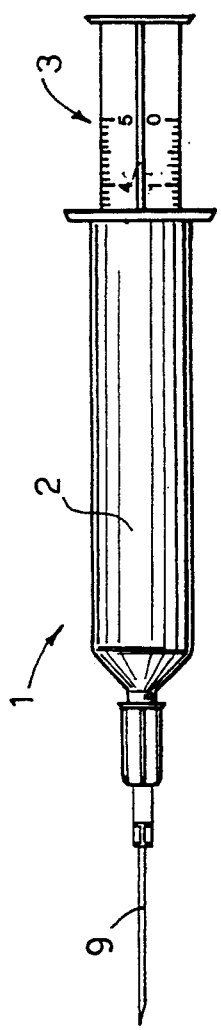

The measuring scales shown in FIGS. 1 to 3 are readable, when numerals are correctly oriented, by persons using the syringe with the right hand. In these Figures it may be clearly seen that the amount of the injected substance can be read directly by the user on the superior scale 6, while the remaining amount can be read on the inferior scale 6'; the opposite happens in case the syringe is used for drawing a substance or during the filling of the same with medicinal substance.

In case of injection for example, in the positions shown in FIGS. 2 and 3, 1.7 and 3.6 ml of substance have been respectively injected (readable on scale 6') and in the syringe respectively remain 2.3 and 1.4 ml of substance. The same happens in case of drawing or filling of the syringe through intake of liquid substance by inverting the function of the two measuring scales 6, 6'.

Figure 4:
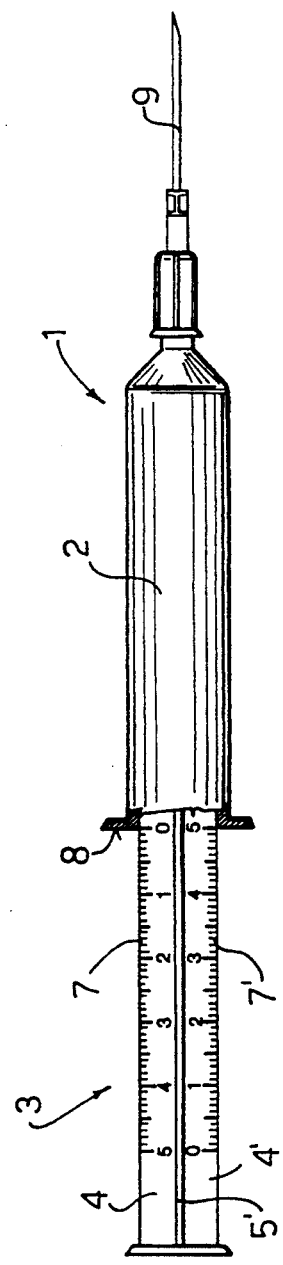
FIG. 4 is a view of the syringe of the previous Figures turned by 180° to show the measuring scales readable by a left handed person.

In FIG. 4, two further measuring scales 7, 7' are foreseen along the sides of wings 4, 4' opposite to those shown in FIGS. 1 to 3, which are also provided with inverted numbering and numerals readable by left handed persons.

Clearly the two further measuring scales 7, 7' may be foreseen also on the second pair of flat wings 5, 5'.

The hypodermic syringe shown in FIGS. 1 to 4 is provided with a metallic needle 9 which, in a way per se known, has an enlarged inserted base 10, also made of metal, enclosed in a plastic bush 11 with inner conical shape, fixed, by means of an interference connection, to a conical tang 12, foreseen on the tip of barrel 2.

According to the present invention, the sleeve base 10 of the needle is lengthened till covering at least ¼ of the length of the needle, in order to stiffen it and limit its tendency to bend. On the needle 9 a protective cap (not shown) is positioned, in a way per se known, and the whole can be packed in a sealed envelope.

Figure 5:
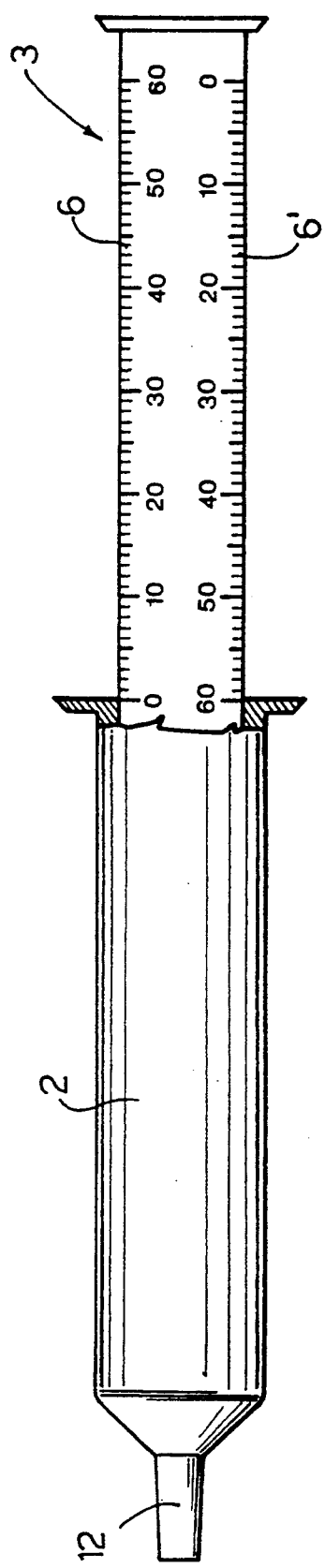
FIGS. 5 and 6 are views of the syringe according to the invention respectively corresponding to those of FIGS. 1 and 4, where the syringe is provided with measuring scales extending up to 60 ml, and is usable for example as a simple pump.
Figure 6:
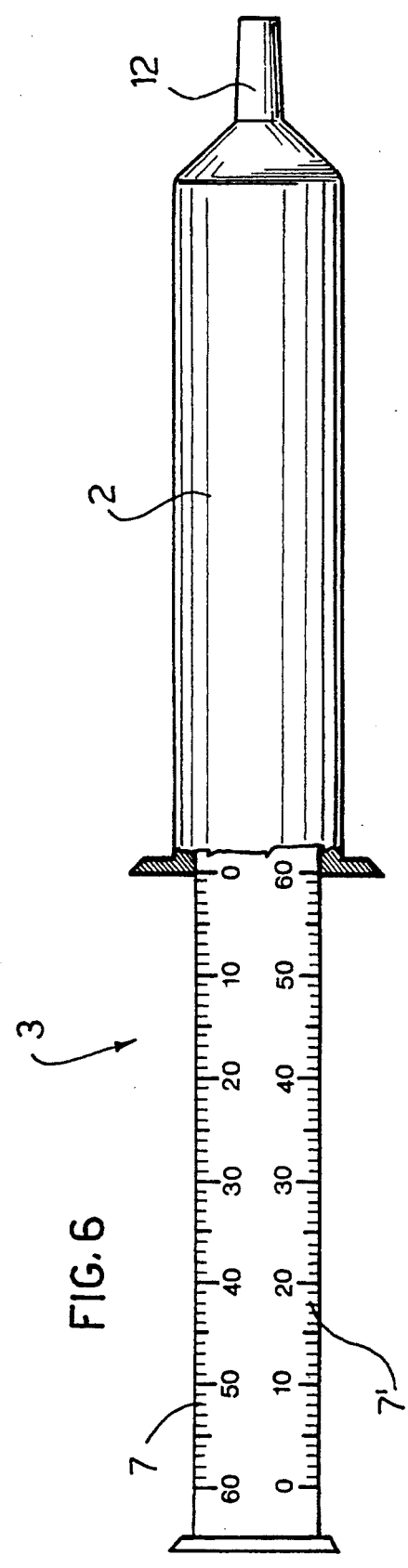

In FIGS. 5 and 6 a 60 ml syringe is shown, which differs from the one in FIGS. 1 to 4 both because of dimensions and the fact that plunger 3 has a cylindrical shape. The four measuring scales 6, 6', 7, 7', with numbering from 0 to 60 are therefore positioned on the outer cylindrical surface of plunger 3. In these FIGS. 5 and 6 the needle is not shown so as to indicate the possibility of using the syringe as a simple pump.

The syringe according to the invention is preferably constructed of plastic material and is of the throw-away type, although the invention clearly also covers other syringes made of more "valuable" materials, which can be used again, provided that the various parts forming the same are sterilized.

While the invention has been illustrated and described herein as embodied in a syringe with blocking capacity, it is not intended to be limited to the details shown, since various modifications and structural changes may be made without departing in any way from the spirit of the present invention.

What I claim is as follows:

1. A disposable syringe for medical use, constructed of plastic material, comprising: a barrel having a base, and a plunger, said barrel being completely opaque, and non-transparent to light, said plunger having at least two measuring scales provided thereon, one with ascending numbering and the other with identical, but descending numbering, said scales having a common index which is made of a rectilinear end of the base of the barrel.

2. The disposable syringe according to claim 1, further comprising two pairs of measuring scales on said plunger, with numbering disposed so as to be readable respectively by a right-handed and a left-handed person.

3. The disposable syringe according to claim 1, wherein said measuring scales are positioned on the plunger by means of one of incision, printing, coloring or application of adhesive strips.

4. The disposable syringe according to claim 1, wherein said plunger has a cross type transverse section, provided with four flat wings placed at right angles with respect to one another, and said measuring scales are placed on at least a pair of said flat wings.

5. The disposable syringe according to claim 1, wherein said plunger is cylindrical and has an external cylindrical surface, and said measuring scales are provided on said cylindrical surface.

6. The disposable syringe according to claim 1, further comprising a metallic needle adapted to be fixed by means of an internally conical bush to a conical tang of the barrel, said needle being covered at its base, with a metallic stiffening sleeve covering at least one-quarter of the length of the needle.

* * * * *